(12) United States Patent
Hossainy

(10) Patent No.: US 9,060,923 B2
(45) Date of Patent: Jun. 23, 2015

(54) METHOD OF TREATING VASCULAR DISEASE IN DIABETIC PATIENTS

(71) Applicant: Abbott Cardiovascular Systems Inc., Sant Clara, CA (US)

(72) Inventor: Syed F. A. Hossainy, Hayward, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 237 days.

(21) Appl. No.: 13/668,019

(22) Filed: Nov. 2, 2012

(65) Prior Publication Data

US 2014/0127278 A1   May 8, 2014

(51) Int. Cl.
*A61F 2/00* (2006.01)
*A61K 9/00* (2006.01)
*A61K 31/56* (2006.01)
*A61K 31/573* (2006.01)

(52) U.S. Cl.
CPC . *A61K 9/00* (2013.01); *A61K 31/56* (2013.01); *A61K 31/573* (2013.01)

(58) Field of Classification Search
CPC ....... A61K 9/00; A61K 31/56; A61K 31/573; A61K 31/436; A61K 38/06; A61P 29/00; A61P 9/00
USPC .......................................................... 424/423
See application file for complete search history.

(56) References Cited

U.S. PATENT DOCUMENTS

| | | | | |
|---|---|---|---|---|
| 7,357,942 B2 * | 4/2008 | Burke et al. | .................. | 424/423 |
| 2009/0286761 A1 * | 11/2009 | Cheng et al. | .................. | 514/171 |
| 2010/0322992 A1 | 12/2010 | Dugan | | |
| 2013/0303496 A1 * | 11/2013 | Cox et al. | ..................... | 514/171 |

FOREIGN PATENT DOCUMENTS

| | | |
|---|---|---|
| EP | 1 588 727 | 10/2005 |
| WO | WO 2004/017892 | 3/2004 |
| WO | WO 2012/047813 | 4/2012 |

OTHER PUBLICATIONS

Lindsay, Jr. et al., "Frequency of major adverse cardiac events within one month of coronary angioplasty: a useful measure of operator performance", J. of the Am. Coll. of Cardiology, 34, pp. 1916-1923 (1999).

"NEVO™ Sirolimus-Eluting Coronary Stent Yields Superior Results to Taxus® Liberte® Stent in Pivotal Clinical Trial", Cordis Corp. 3 pgs (2009).

Costa et al., "The randomised study of the double dose versus single dose sirolimus-eluting stent for the treatment of diabetic patients with de novo coronary lesions", EuroInterv. 2, pp. 295-301 (2006).

Grunberg et al., "Diabetes and Sirolimus-Eluting Stent Trial", Medscape, downloaded from: www.medscape.com/viewarticle/491691, Jun. 4, 2012, 4 pgs.

Cutlip et al., "Beyond Restenosis: Five-Year Clinical Outcomes from Second-Generation Coronary Stent Trials", Circulation 110, pp. 1226-1230 (2004).

"Target Lesion Revascularization After Bare-Metal of DES: Results", downloaded from: www.medscape.com/viewarticle/724849, May 30, 2012, 2 pgs.

Costa "Significance of Late Loss and Target Lesion Revascularization in Interperting Drug-Eluting Stent Clinical Trial Results", Div. of Cardiology, Univ. of Florida, 4 pgs. (2008).

Ellis et al., "Relationship between angiographic late loss and target lesion revascularization after coronary stent implantation", J. of the Am. Coll. of Cardiology 45, pp. 1193-1200 (2005).

International Search Report for PCT/US2013/060175, mailed Jan. 20, 2014, 9 pgs.

* cited by examiner

*Primary Examiner* — Suzanne Ziska
(74) *Attorney, Agent, or Firm* — Squire Patton Boggs (US) LLP

(57) ABSTRACT

The present invention relates to the treatment of vascular disease in a diabetic patient using a drug-eluting implantable medical device that releases everolimus from three distinctly loaded drug reservoir layers wherein at least one of the layers comprises at least 200 µg/cm² of everolimus and further wherein the everolimus is the only therapeutic agent in the layers or the layers or any combination thereof further comprise an anti-inflammatory agent or an RGD peptide or both.

17 Claims, No Drawings

METHOD OF TREATING VASCULAR DISEASE IN DIABETIC PATIENTS

FIELD

The present invention relates to a method of treating vascular disease in diabetic patients that reduces the incidence of early stage (approximately one year or less post-implantation) target lesion revascularization (TLR) and ensuing additional major adverse cardiac events (MACE). The method comprises staged administration of at least three distinct timed-release doses of an mTOR inhibitor, one or more of which doses are substantially higher than those currently indicated for commercial mTOR inhibitors.

BACKGROUND

Until the mid-1980s, the accepted treatment for coronary atherosclerosis, i.e., narrowing of the coronary artery(ies) was coronary by-pass surgery. While being quite effective and having evolved to a relatively high degree of safety for such an invasive procedure, by-pass surgery still involves potentially serious complications and generally results in an extended recovery period.

With the advent of percutaneous transluminal coronary angioplasty (PTCA) in 1977, the scene changed dramatically. Using catheter techniques originally developed for heart exploration, inflatable balloons were deployed to re-open occluded regions in arteries. The procedure was relatively non-invasive, took a very short time compared to by-pass surgery and the recovery time was minimal. However, PTCA brought with it other problems such as vasospasm and elastic recoil of the stretched arterial wall which could undo much of what was accomplished and, in addition, engendered a new problem, restenosis, the re-clogging of the treated artery due to neointimal hyperplasia.

The next improvement, advanced in the mid-1980s, was the use of a stent to maintain luminal diameter after being re-established using PTCA. This for all intents and purposes put an end to vasospasm and elastic recoil but did not resolve the issue of restenosis. That is, prior to the introduction of stents, restenosis occurred in from about 30 to 50% of patients undergoing PTCA. Stenting reduced this to about 15 to 20%, a substantial improvement but still more than desirable.

In 2003, the drug-eluting stent (DES) was introduced. The drugs initially used with DESs were cytostatic compounds, that is, compounds that curtailed the proliferation of cells that resulted in restenosis. The occurrence of restenosis was reduced to about 5 to 7%, a relatively acceptable figure. However, the use of DESs engendered yet another complication, late stent thrombosis, the forming of blood clots long after the stent was in place. It was hypothesized that the formation of blood clots was most likely due to delayed healing, a side-effect of the use of cytostatic drugs.

It was found that the physiopathology of restenosis involves early injury to smooth muscle cells (SMCs), de-endothelialization and thrombus deposition. Over time, this leads to SMC proliferation and migration and extra-cellular matrix deposition. There is an increasing body of evidence suggesting that inflammation plays a pivotal role in linking this early vascular injury with neointimal growth and eventual lumen compromise, i.e., restenosis. Further, it has been observed that, when stents are used, the inflammatory state if often more intense and prolonged, exacerbating the situation.

To deal with the above, dual-drug DESs are being developed which comprise an anti-proliferative drug to combat SMC proliferation and an anti-inflammatory drug to reduce inflammation. A particularly noteworthy family of anti-proliferative drugs is the mammalian target of rapamycin (mTOR) inhibitor family. mTOR inhibitors mitigate restenosis through inhibition of smooth muscle cell growth. mTORs are, however, non-specific and also inhibit the growth of endothelial cells, which has been suggested to possibly slow the overall healing process.

Inflammation is, of course, a normal response to injury and is necessary for the healing process. However, chronic inflammation can be detrimental to healing in that the constant recruitment of monocytes, lymphocytes and neutrophils leads to a constant generation of inflammatory cytokines along with reactive oxygen species and enzymes generated by inflammatory cells to remove foreign bodies or damaged tissue. Thus, anti-inflammatory drugs are often included in dual drug DESs to control chronic inflammation by reducing cytokine-driven neotintimal growth. Long-term administration of anti-inflammatory drugs, however, can shut down the healing process completely.

While generally effective, current single- and dual-drug DESs have not completely served certain patient groups. For example, in the SIRIUS clinical trial, patients with diabetes were roughly twice as likely as non-diabetics to incur binary restenosis. Further, diabetic patients tend to be more prone, post vascular repair surgery, to major adverse cardiac events (MACE). It has been observed, however, that increased MACE events such as acute myocardial infarction (AMI), thrombosis and cardiac death in diabetics during approximately the first year post stent placement correlate with target lesion revascularization (TLR) rather than with non-TLR-related causes. TLR, in turn, correlates well with the presence of restenosis in, closely proximal to or closely distal to, the target lesion. Thus it appears that current DES regimes do not adequately service the needs of diabetic patients suffering from vascular diseases.

What is needed is a method of treating vascular disease in diabetics that addresses the risk of TLR and attendant MACE. This invention provides such a method.

SUMMARY

Thus, in one aspect, this invention relates to an implantable medical device for treatment of vascular disease in a diabetic patient, comprising:
a device body;
optionally, a primer layer disposed over the device body;
three drug reservoir layers disposed over the device body, wherein each layer comprises everolimus and at least one of the three reservoir layers comprises at least 200 µg/cm$^2$ of everolimus; wherein
  the first drug reservoir layer, which is the outermost of the drug reservoir layers, releases at least 90% of the everolimus over about 7 days post implantation of the device;
  the second drug reservoir layer, which is disposed beneath the first drug reservoir layer, releases at least 90% of the everolimus over about 22 days beginning at about day 8 post implantation of the device; and
  the third drug reservoir layer, which is disposed beneath the second drug reservoir layer, releases at least 90% of the everolimus over about 150 days beginning at about day 30 post implantation.

In an aspect of this invention, the first drug reservoir layer comprises about 100 µg/cm$^2$ to about 200 µg/cm$^2$ of everolimus; the second drug reservoir layer comprises about 200

µg/cm² to about 800 µg/cm² everolimus; and the third drug reservoir layer comprises about 20 to about 100 µg/cm² of everolimus.

In an aspect of this invention, the first drug reservoir layer comprises about 100 µg/cm² of everolimus; the second drug reservoir layer comprises about 500 µg/cm² of everolimus; and the third drug reservoir layer comprises about 100 µg/cm² of everolimus.

In an aspect of this invention, the first drug reservoir layer comprises about 200 µg/cm² of everolimus; the second drug reservoir layer comprises about 300 µg/cm² of everolimus; and the third drug reservoir layer comprises about 20 µg/cm² of everolimus.

In an aspect of this invention, the implantable medical device further comprises an anti-inflammatory agent in the first drug reservoir layer, in the second drug reservoir layer, in the third drug reservoir layer or in any combination thereof.

In an aspect of this invention, the anti-inflammatory agent is selected from the group consisting of dexamethasone and clobetasol.

In an aspect of this invention, the implantable medical device further comprises and RGD peptide, a c-RGD peptide or an RGD peptide mimetic in the first drug reservoir layer, in the second drug reservoir layer, in the third drug reservoir layer or in any combination thereof.

In an aspect of this invention, the implantable medical device further comprises a barrier layer between the first drug reservoir layer and the external environment, between the first drug reservoir layer and the second drug reservoir layer, between the second drug reservoir layer and the third drug reservoir layer or any combination of the foregoing.

In an aspect of this invention, the implantable medical device comprises a stent.

An aspect of this invention is a method for treating a vascular disease in a diabetic patient, comprising:
delivering an implantable medical device to or near the diseased region of the vasculature wherein the device comprises three drug reservoir layers, at least one of which comprises at least 200 µg/cm² of everolimus;
releasing 90% or more of everolimus contained in a first drug reservoir layer, which is the outermost drug reservoir layer, over the first 7 days post implantation;
releasing 90% or more of everolimus contained in a second drug reservoir, which is disposed beneath the first drug reservoir layer, over about 22 days beginning on about day 8 post implantation; and
releasing 90% or more of everolimus contained in a third drug reservoir, which is disposed beneath the second drug reservoir layer, over about 150 days beginning on about day 30 post implantation.

In an aspect of this invention, in the above method the first drug reservoir layer comprises about 100 µg/cm² to about 200 µg/cm² of everolimus; the second drug reservoir layer comprises about 200 µg/cm² to about 800 µg/cm² everolimus; and the third drug reservoir layer comprises about 20 to about 100 µg/cm² of everolimus.

In an aspect of this invention, in the above method the first drug reservoir layer comprises about 100 µg/cm² of everolimus; the second drug reservoir layer comprises about 500 µg/cm² of everolimus; and the third drug reservoir layer comprises about 100 µg/cm² of everolimus.

In an aspect of this invention, in the above method, the first drug reservoir layer comprises about 200 µg/cm² of everolimus; the second drug reservoir layer comprises about 300 µg/cm² of everolimus; and the third drug reservoir layer comprises about 20 µg/cm² of everolimus.

In an aspect of this invention, the above method further comprises releasing an anti-inflammatory agent from the first drug reservoir layer, from the second drug reservoir layer, from the third drug reservoir layer or from any combination thereof over the same time interval as the everolimus release from each drug reservoir layer.

In an aspect of this invention, in the above method, the anti-inflammatory agent is selected from the group consisting of clobetasol and dexamethasone.

In an aspect of this invention, the above method further comprises releasing an RGD peptide, a c-RGD peptide or an RGD peptide mimetic from the first drug reservoir layer, from the second drug reservoir layer, from the third drug reservoir layer or from any combination thereof over the same time interval as the everolimus release from each drug reservoir layer.

In an aspect of this invention, in the above method, the implantable medical device is a stent.

DETAILED DESCRIPTION

It is understood that use of the singular throughout this application including the claims includes the plural and vice versa unless expressly stated otherwise. That is, "a" and "the" are to be construed as referring to one or more of whatever the word modifies. Non-limiting examples are: "an anti-inflammatory agent," which is understood to include one or more such agents, and "a drug reservoir layer," which is understood to include one or more such layers, unless it is expressly stated or is unambiguously obvious from the context that such is not intended.

As used herein, words of approximation such as, without limitation, "about," "substantially," "essentially" and "approximately" mean that the word or phrase modified by the term need not be exactly that which is written but may vary from that written description to some extent. The extent to which the description may vary will depend on how great a change can be instituted and still have one of ordinary skill in the art recognize the modified version as still having the properties, characteristics and capabilities of the modified word or phrase. In general, but subject to the preceding discussion, a numerical value herein that is modified by a word of approximation may vary from the stated value by about ±15%.

As used herein, the use of "preferred," "preferably," or "more preferred," and the like refer to preferences as they existed at the time of filing of the patent application.

As used herein, "optional" means that the element modified by the term may, but is not required to, be present.

As used herein, "drug," "therapeutic agent" and "agent" are interchangeable and refer to a pharmacological substance use to treat a disease or disorder.

It is generally known that diabetics often present with more complex coronary lesions that tend to be more challenging to treat due to various diabetic complications. Treatment of vascular lesions in diabetics, however, has been slow in developing even though the restenosis rate in diabetics is currently in double digits, especially for longer lesions, while for nondiabetic patients the restenosis rate can be as low as 1.8%. It is currently estimated by the Center for Disease Control and Prevention (CDC) that one in ten Americans has diabetes in some form. The prediction for the future is not encouraging in that the CDC predicts that, by 2050, one in three Americans will have diabetes. While efforts are being made to lower these numbers by lifestyle and dietary changes, most likely such efforts will have a limited impact. Due to the large fraction of the general populace already afflicted with diabetes and the prediction of an even higher proportion in the future, treatments directed toward diabetics is much needed.

Target lesion revascularization (TLR) refers to a re-intervention, e.g., by percutaneous revascularization or surgical bypass, performed for ≥50% diameter stenosis, which is confirmed by angiography, within ±5 mm proximal and/or distal to the target lesion after documentation of recurrent clinical symptoms of peripheral arterial disease following the initial procedure. The clinical symptoms can include, without limitation, ischemic symptoms or a positive functional ischemia study. Diabetes has been found to be a strong predictor of short-term restenosis. It is the intent of this invention to reduce occurrence of short-term restenosis and concomitantly reduce the need for TLR with its attendant risk of MACE in diabetic patients.

As used herein, an "implantable medical device" refers to any type of appliance that is totally or partly introduced, surgically or medically, into a patient's body or by medical intervention into a natural orifice, and which is intended to remain there after the procedure. The duration of implantation may be essentially permanent, i.e., intended to remain in place for the remaining lifespan of the patient; until the device biodegrades; or until it is physically removed. Examples of implantable medical devices include, without limitation, implantable cardiac pacemakers and defibrillators; leads and electrodes for the preceding; implantable organ stimulators such as nerve, bladder, sphincter and diaphragm stimulators, and cochlear implants; prostheses, vascular grafts, self-expandable stents, balloon-expandable stents, stent-grafts, grafts, artificial heart valves, patent foramen ovale closure devices, left atrial appendage excluders, and cerebrospinal fluid shunts.

As used herein, "device body" refers to a fully formed implantable medical device with an outer surface to which no coating or layer of material different from that of which the device itself is manufactured has been applied. By "outer surface" is meant any surface however spatially oriented that would be in contact with bodily tissue or fluids if the device were implanted in a patinet. A common example of a "device body" is a BMS, i.e., a bare metal stent, which is a fully-formed usable stent that has not been coated on any surface that is in contact with bodily tissue or fluids with a layer of any material different from the metal of which it is made. "Device body" refers not only to BMSs but to any uncoated device regardless of what material it is made. For example, without limitation, the preceding definition would apply equally to polymeric stent bodies.

Presently preferred implantable medical devices of this invention are stents. A stent refers generally to any device used to hold tissue in place in a patient's body. Very often, stents are employed for the localized delivery of therapeutic agents to one or more specific treatment sites in a patient's body. Particularly useful stents are those used for the maintenance of the patency of a vessel in a patient's body when the vessel is narrowed or closed due to diseases or disorders including, without limitation, tumors (in, for example, bile ducts, the esophagus, the trachea/bronchi, etc.), benign pancreatic disease, coronary artery disease, carotid artery disease and peripheral arterial disease such as atherosclerosis, restenosis and vulnerable plaque. Vulnerable plaque (VP) refers to a fatty build-up in an artery thought to be caused by inflammation. The VP is covered by a thin fibrous cap that can rupture leading to blood clot formation. A stent can be used to strengthen the wall of the vessel in the vicinity of the VP and act as a shield against such rupture. A stent can be used in, without limitation, neuro, carotid, coronary, pulmonary, aorta, renal, biliary, iliac, femoral and popliteal as well as other peripheral vasculatures. A stent can be used in the treatment or prevention of disorders such as, without limitation, thrombosis, restenosis, hemorrhage, vascular dissection or perforation, vascular aneurysm, chronic total occlusion, claudication, anastomotic proliferation, bile duct obstruction and ureter obstruction.

A stent used for patency maintenance is usually delivered to the target site in a compressed state and then expanded to fit the vessel into which it has been inserted. Once at a target location, a stent may be self-expandable or balloon expandable.

As used herein, a "primer layer" refers to a coating consisting of a polymer or blend of polymers that exhibit good adhesion characteristics with regard to the material of which the device body is manufactured and good adhesion characteristics with regard to whatever material is to be coated on the device body. Thus, a primer layer serves as an intermediary layer between a device body and materials to be affixed to the device body and is, therefore, applied directly to the device body. Examples of primers, without limitation, include acrylate and methacrylate polymers with poly(n-butyl methacrylate) (PBMA) being a presently preferred primer. Some additional examples of primers include, but are not limited to, poly(ethylene-co-vinyl alcohol), poly(vinyl acetate-co-vinyl alcohol), poly(methacrylates), poly(acrylates), polyethyleneamine, polyallylamine, chitosan, poly(ethylene-co-vinyl acetate), and parylene-C.

As use herein, a material that is described as a layer "disposed over" an indicated substrate, e.g., without limitation, a device body or another layer, refers to a relatively thin coating of the material applied, preferably at present, directly to essentially the entire exposed surface of the indicated substrate. By "exposed surface" is meant any surface regardless of its physical location with respect to the configuration of the device that, in use, would be in contact with bodily tissues or fluids. "Disposed over" may, however, also refer to the application of the thin layer of material to an intervening layer that has been applied to the substrate, wherein the material is applied in such a manner that, were the intervening layer not present, the material would cover substantially the entire exposed surface of the substrate. Thus, a "first drug reservoir layer" that is disposed "over the device body" includes both deposition of the drug reservoir layer directly onto the device body or onto a primer layer that was previously applied to the device body.

As used herein, "drug reservoir layer" refers either to a layer of one or more therapeutic agents applied neat or to a layer of polymer or blend of polymers that has dispersed within its three-dimensional structure one or more therapeutic agents. A polymeric drug reservoir layer is designed such that, by one mechanism or another, e.g., without limitation, by elution or as the result of biodegradation of the polymer, the therapeutic substance is released from the layer into the surrounding environment. For the purpose of this invention, the drug reservoir layer may act as a rate-controlling layer that metes out the therapeutic agent over a predetermined time.

As used herein, a "barrier layer" refers to a polymer layer that is disposed between a drug reservoir layer and the external environment or between two drug reservoir layers. With regard to the former use, the barrier layer may act simply as a protective layer between the external environment and the drug reservoir layer. When the device is implanted in a patient the barrier layer is relatively rapidly decomposed, exposing the drug reservoir layer. In addition, this barrier layer may provide a release rate element that controls the time of release of an agent from the outermost drug reservoir layer into the external environment. On the other hand, a barrier layer that is placed between drug reservoir layers may also perform two functions. As in the preceding discussion, the barrier layer may act as a release rate element for the agent below it. Or the barrier layer may be substantially impenetrable to the agents in the layers beneath it such that the agents cannot migrate to layers other than the one in which they were initially incorporated until the barrier layer is brought into contact with bodily fluids, at which time the barrier becomes fully penetrable by the agents. In the latter instance, the barrier layers ensure that agents in each layer stay put during storage of the device until the device is put into use and thereby ensure that the intended distinct, separate doses of agents are released form the device in accordance with teachings of this disclosure.

As used herein, an "outermost" drug reservoir layer simply refers to the drug reservoir layer that is nearest the external environment compared to the other drug reservoir layers. It is not necessarily the case that the outermost layer is in fact itself in contact with the external environment; there may be additional layers between the outermost drug reservoir layer and the environment.

As used herein, a layer that is "beneath" another layer refers to a layer that is further from the external environment that the layer which it is beneath. It is not necessarily so that the layer that is beneath another layer is in contact with the layer between it and the external environment; there may be other layers between the two layers.

As used herein, "agent," "therapeutic agent" or "drug" refers to any substance that, when administered in a therapeutically effective amount to a patient suffering from a disease, has a therapeutic beneficial effect on the health and well-being of the patient. A therapeutic beneficial effect on the health and well-being of a patient includes, but it not limited to: (1) curing the disease; (2) slowing the progress of the disease; (3) causing the disease to retrogress; or, (4) alleviating one or more symptoms of the disease. As used herein, a therapeutic agent also includes any substance that when administered to a patient, known or suspected of being particularly susceptible to a disease, in a prophylactically effective amount, has a prophylactic beneficial effect on the health and well-being of the patient. A prophylactic beneficial effect on the health and well-being of a patient includes, but is not limited to: (1) preventing or delaying on-set of the disease in the first place; (2) maintaining a disease at a retrogressed level once such level has been achieved by a therapeutically effective amount of a substance, which may be the same as or different from the substance used in a prophylactically effective amount; or, (3) preventing or delaying recurrence of the disease after a course of treatment with a therapeutically effective amount of a substance, which may be the same as or different from the substance used in a prophylactically effective amount, has concluded.

As used herein, "treating" refers to the administration of a therapeutically effective amount of a therapeutic agent to a patient known or suspected to be afflicted with a vascular disease.

A "therapeutically effective amount" refers to that amount of a therapeutic agent that will have a beneficial effect, which may be curative or palliative, on the health and well-being of the patient with regard to the vascular disease with which the patient is known or suspected to be afflicted. With regard to this invention, multiples of currently approved mTOR inhibitor doses are administered to eliminate or at least substantially reduce the need for TLR and its attendant risks.

As used herein, a "diabetic patient" refers primarily to a human being that presents with diagnosed type 1 or type 2 diabetes mellitus. In addition, however, for the purposes of this invention a "diabetic patient" also refers to one who, while not necessarily exhibiting all the characteristic of full-blown diabetes, presents with a compromised vasculature that exhibits the negative characteristics associated with a patient suffering from diagnosed type 1 or type 2 diabetes.

As used herein, a "vascular disease" refers to a disease of the vessels, primarily arteries and veins, which transport blood to and from the heart, brain and peripheral organs such as, without limitation, the arms, legs, kidneys and liver. In particular "vascular disease" refers to the coronary arterial and venous systems, the carotid arterial and venous systems, the aortic arterial and venous systems and the peripheral arterial and venous systems. The disease that may be treated is any that is amenable to treatment with a therapeutic agent, either as the sole treatment protocol or as an adjunct to other procedures such as surgical intervention. The disease may be, without limitation, atherosclerosis, vulnerable plaque, restenosis or peripheral arterial disease. Peripheral vascular disease includes arterial and venous diseases of the renal, iliac, femoral, popliteal, tibial and other vascular regions.

Peripheral vascular diseases are generally caused by structural changes in blood vessels caused by such conditions as inflammation and tissue damage. A subset of peripheral vascular disease is peripheral artery disease (PAD). PAD is a condition that is similar to carotid and coronary artery disease in that it is caused by the buildup of fatty deposits on the lining or intima of the artery walls. Just as blockage of the carotid artery restricts blood flow to the brain and blockage of the coronary artery restricts blood flow to the heart, blockage of the peripheral arteries can lead to restricted blood flow to the kidneys, stomach, arms, legs and feet. In particular at present a peripheral vascular disease often refers to a vascular disease of the superficial femoral artery.

A "vascular lesion" refers to a localized pathological change in the vasculature, in particular a change that results in compromising the patency of the vasculature in the vicinity of the lesion. A vascular lesion may occur in any vascular region including, without limitation, arteries and veins in the carotid, aortic, renal, iliac, femoral, popliteal and tibial vasculature. Specific examples of vascular lesions include, without limitation, saphenous vein graft lesions, restenotic lesions, bifurcation lesions, ostial lesions, left main lesions, chronic total occlusions and occlusions associated with AMI (Acute Myocardial Infarction) or STEMI (ST-segment Elevation Myocardial Infarction).

"Atherosclerosis" refers to the depositing of fatty substances, cholesterol, cellular waste products, calcium and fibrin on the inner lining or intima of an artery. Smooth muscle cell proliferation and lipid accumulation accompany the deposition process. In addition, inflammatory substances that tend to migrate to atherosclerotic regions of an artery are thought to exacerbate the condition. The result of the accumulation of substances on the intima is the formation of fibrous (atheromatous) plaques that occlude the lumen of the artery, a process called stenosis. When the stenosis becomes severe enough, the blood supply to the organ supplied by the particular artery is depleted resulting in a stroke, if the afflicted artery is a carotid artery, heart attack if the artery is coronary, or loss of organ or limb function if the artery is peripheral.

"Restenosis" refers to the re-narrowing of an artery at or near the site where angioplasty or another surgical procedure was previously performed to remove a stenosis. It is generally due to smooth muscle cell proliferation and, at times, is accompanied by thrombosis. Prior to the advent of implantable stents to maintain the patency of vessels opened by angioplasty, restenosis occurred in 40-50% of patients within 3 to 6 months of undergoing the procedure. Post-angioplasty restenosis before stents was due primarily to smooth muscle cell proliferation. However, there were also issues of acute re-closure due to vasospasm, dissection, and thrombosis at the site of the procedure. Stents eliminated acute closure from vasospasm and greatly reduced complications from dissections. The use of IIb-IIIa anti-platelet drugs such as abciximab and epifabatide, and anti-platelet agents such as ticlopidine and clopidogrel, which are anti-thrombotic, reduced the occurrence of post-procedure clotting. Stent placement sites are also susceptible to restenosis due to abnormal tissue growth at the site of implantation. This form of restenosis tends also to occur at 3 to 6 months after stent placement but it is not affected by the use of anti-clotting drugs. This appears to be especially so with diabetic patients. Thus, alternative therapies are continuously being sought to mitigate, preferably eliminate, this type of restenosis, in particular for diabetic patients. As mentioned previously, this invention provides a DES treatment that is expected to resolve the early restenosis issue with regard to diabetic patients.

"Vulnerable plaque" refers to an atheromatous plaque that has the potential of causing a thrombotic event and is usually characterized by a thin fibrous cap separating a lipid filled atheroma from the lumen of an artery. The thinness of the cap renders the plaque susceptible to rupture. When the plaque ruptures, the inner core of usually lipid-rich plaque is exposed to blood. This releases tissue factor and lipid components with the potential of causing a potentially fatal thrombotic event through adhesion and activation of platelets and plasma proteins to components of the exposed plaque.

The phenomenon of "vulnerable plaque" has created new challenges in recent years for the treatment of heart disease. Unlike occlusive plaques that impede blood flow, vulnerable plaque develops within the arterial walls, and in its early stages does so without the characteristic substantial narrowing of the arterial lumen which produces symptoms. As such, conventional methods for detecting heart disease, such as an angiogram, may not detect vulnerable plaque growth into the arterial wall.

"Thrombosis" refers to the formation or presence of a blood clot (thrombus) inside a blood vessel or chamber of the heart. A blood clot that breaks off and travels to another part of the body is called an embolus. If a clot blocks a blood vessel that feeds the heart, it causes a heart attack. If a clot blocks a blood vessel that feeds to brain, it causes a stroke.

As used herein, "eluting" refers to the exodus of an agent from a drug reservoir layer into the external environment. The "external environment" for an implantable medical device in use will in generaly constitute the interior of a patient's body, most often the interior of a lumen of a vessel in that patient.

Prevention, or at least the reduction of, early stage restenosis has been found to be highly correlated with administration of antiproliferative agents that curtail SMC growth and migration. Thus, it is an embodiment of this invention to administer relatively large doses of such agents to more effectively reduce the proliferation of SMCs in diabetics post stent implantation.

For the purposes of this invention, the preferred antiproliferative agents are mTOR inhibitors such as, without limitation, everolimus, zotarolimus, sirolimus, biolimus, myolimus, novolimus, temsirolimus, deforolimus and combinations thereof, with everolimus being the presently preferred mTOR inhibitor for use in the method of this invention. Everolimus is a semi-synthetic derivative of rapamycin, a naturally product isolated from *Streptomyces hydroscopicus*, and is prepared by substituting a 2-hydroxyethoxy moiety for the hydroxyl group at position 42 of rapamycin.

Everolimus is quite hydrophobic, which is an advantageous property with regard to delivery of the compound from a drug reservoir layer of a stent. That is, the compound's hydrophobicity permits slow sustained release from a hydrophobic polymer, which in turn facilitates maintenance of therapeutic drug levels eluting from the drug reservoir layer of the stent. Very low water solubility also leads to a long residence time in tissues. Further, its lipophilic character favors crossing of cell membranes to inhibit neointimal proliferation of target tissues.

The currently approved dose density of everolimus on an implantable medical device, in particular on a stent, is approximately 100 $\mu g/cm^2$. While such dose density has been proven to be effective in reducing early stage restenosis in non-diabetic patients, it does not show as marked an effect with used in diabetics due, it is believed, to the compromised nature of the diabetic vasculature. Thus, it is an embodiment of this invention to administer substantially larger doses of everolimus to diabetic patients in a sequential pattern from a DES.

In the discussion that follows, this invention will be described in terms of the presently preferred mTOR inhibitor, everolimus, and a stent (DES) as the implantable medical device. It is understood, however, that, based on the disclosure herein, it will be apparent to those skilled in the art how to apply the teachings herein to the use of other mTOR inhibitors for which the dose density for treatment of non-diabetic patients is or becomes known and to other implantable medical devices. Such mTOR inhibitors and devices are, therefore, within the scope of this invention.

Thus, in an embodiment of this invention, everolimus will be contained in at least three polymeric drug reservoir layers on a stent. The layers are formulated such that they release everolimus over distinctly different time intervals, which can be classified as early, mid and late release. Early release refers to release during the first 7 days post-implantation of the stent. Mid release refers to release from about day 8 to about day 29 post implant. Late release refers to release from about day 30 to about day 180 post implant. At least one of these release events involves a drug reseroir layer containing from a 2- to 8-fold greater dose density reservoir layer than in currently approved protocols. With regard to everolimus, as mentioned previously, the current approved dose density is about 100 $\mu g/cm^2$, which translates to about 200 to about 800 $\mu g/cm^2$ of everolimus in at least one drug reservoir layer for the purpose of this invention. A non-limiting example would be a stent having an outermost drug reservoir layer loaded with 100 $\mu g/cm^2$ of everolimus, a 500 $\mu g/cm^2$ drug reservoir layer beneath the outermost layer and another 100 $\mu g/cm^2$ everolimus innermost drug reservoir layer. Another non-limiting example would be an outermost drug reservoir layer containing about 200 $\mu g/cm^2$ everolimus, a mid-reservoir layer containing about 300 $\mu g/cm^2$ of everolimus and an innermost drug reservoir layer containing about 20 $\mu g/cm^2$ everolimus. It is to be understood that the exact dose densities of each of the at least three drug reservoir layers are not intended nor are they to be construed as being limited by this disclosure. The key element of this invention is the early administration of enhanced quantities of everolimus or another of the previously identified mTOR inhibitors through the use of higher than currently approved dose density drug reservoir layers on a stent or other implantable medical device.

The timing of the release of the mTOR inhibitor from the drug reservoir layers will depend on several well-known parameters. First, and perhaps foremost, is the composition of the drug reservoir layers, that is, the polymers that comprise the layers.

A polymer for use in a drug reservoir layer of this invention must be biocompatible. As used herein, "biocompatible" refers to a polymer that both in its intact as synthesized state and in its decomposed state, i.e., its degradation products, is not, or at least is minimally toxic to living tissue; does not, or at least minimally and reparably injures living tissue; and/or does not, or at least minimally and/or controllably causes an immunological reaction in living tissue.

Biocompatible polymers of this invention may be biostable. Biostable means that the polymer is unaffected by the conditions and substances in a patient's body such as pH, the presence of enzymes, body temperature, etc. That is, the polymer maintains its initial composition, molecular weight, etc. Conversely, biodegradable means that the polymer will be decomposed over time when exposed to the aforesaid physiological environs.

Examples of biocompatible, biostable polymers that may be used in drug reservoir layers of this invention include, without limitation, polyacrylates, polymethacryates, polyureas, polyurethanes, polyolefins, polyvinylhalides, polyvinylidenehalides, polyvinylethers, polyvinylaromatics, polyvinylesters, polyacrylonitriles, polysiloxanes, alkyd resins and epoxy resins.

Biocompatible, biodegradable polymers include naturally-occurring polymers such as, without limitation, collagen, chitosan, alginate, fibrin, fibrinogen, cellulosics, starches, dextran, dextrin, hyaluronic acid, heparin, glycosaminoglycans, polysaccharides and elastin.

Synthetic polymers, that is, polymers that are created wholly in the laboratory, and semi-synthetic polymers, naturally-occurring polymers that have been chemically modified in the laboratory that can be used to formulate the drug reservoir layers of this invention include, without limitation, polyphosphazines, polyphosphoesters, polyphosphoester urethane, polyhydroxyacids, polyhydroxyalkanoates, polyanhydrides, polyesters, polyorthoesters, polyamino acids, polyoxymethylenes, poly(ester-amides) and polyimides.

Other biocompatible biodegradable polymers that may be used with the device and method of this invention include, without limitations, polyesters, polyhydroxyalkanoates (PHAs), poly(ester amides) that may optionally contain alkyl, amino acid, PEG and/or alcohol groups, polycaprolactone, poly(L-lactide), poly(D,L-lactide), poly(D,L-lactide-co-PEG) block copolymers, poly(D,L-lactide-co-trimethylene carbonate), polyglycolide, poly(lactide-co-glycolide), polydioxanone (PDS), polyorthoester, polyanhydride, poly(glycolic acid-co-trimethylene carbonate), polyphosphoester, polyphosphoester urethane, poly(amino acids), polycyanoacrylates, poly(trimethylene carbonate), poly(iminocarbonate), polycarbonates, polyurethanes, copoly(ether-esters) (e.g. PEO/PLA), polyalkylene oxalates, polyphosphazenes, PHA-PEG, and combinations thereof. The PHA may include poly($\alpha$-hydroxyacids), poly($\beta$-hydroxyacid) such as poly(3-hydroxybutyrate) (PHB), poly(3-hydroxybutyrate-co-valerate) (PHBV), poly(3-hydroxyproprionate) (PHP), poly(3-hydroxyhexanoate) (PHH), or poly(4-hydroxyacid) such as poly poly(4-hydroxybutyrate), poly(4-hydroxyvalerate), poly(4-hydroxyhexanoate), poly(hydroxyvalerate), poly(tyrosine carbonates), poly(tyrosine arylates), poly(ester amide), polyhydroxyalkanoates (PHA), poly(3-hydroxyalkanoates) such as poly(3-hydroxypropanoate), poly(3-hydroxybutyrate), poly(3-hydroxyvalerate), poly(3-hydroxyhexanoate), poly(3-hydroxyheptanoate) and poly(3-hydroxyoctanoate), poly(4-hydroxyalkanaote) such as poly (4-hydroxybutyrate), poly(4-hydroxyvalerate), poly(4-hydroxyhexanote), poly(4-hydroxyheptanoate), poly(4-hydroxyoctanoate) and copolymers including any of the 3-hydroxyalkanoate or 4-hydroxyalkanoate monomers described herein or blends thereof, poly(D,L-lactide), poly (L-lactide), polyglycolide, poly(D,L-lactide-co-glycolide), poly(L-lactide-co-glycolide), polycaprolactone, poly(lactide-co-caprolactone), poly(glycolide-co-caprolactone), poly(dioxanone), poly(ortho esters), poly(anhydrides), poly (tyrosine carbonates) and derivatives thereof, poly(tyrosine ester) and derivatives thereof, poly(imino carbonates), poly (glycolic acid-co-trimethylene carbonate), polyphosphoester, polyphosphoester urethane, poly(amino acids), polycyanoacrylates, poly(trimethylene carbonate), poly (iminocarbonate), polyphosphazenes, silicones, polyesters, polyolefins, polyisobutylene and ethylene-alphaolefin copolymers, acrylic polymers and copolymers, vinyl halide polymers and copolymers, such as polyvinyl chloride, polyvinyl ethers, such as polyvinyl methyl ether, polyvinylidene halides, such as polyvinylidene chloride, polyacrylonitrile, polyvinyl ketones, polyvinyl aromatics, such as polystyrene, polyvinyl esters, such as polyvinyl acetate, copolymers of vinyl monomers with each other and olefins, such as ethylene-methyl methacrylate copolymers, acrylonitrile-styrene copolymers, ABS resins, and ethylene-vinyl acetate copolymers, polyamides, such as Nylon 66 and polycaprolactam, alkyd resins, polycarbonates, polyoxymethylenes, polyimides, polyethers, poly(glyceryl sebacate), poly(propylene fumarate), poly(n-butyl methacrylate), poly(sec-butyl methacrylate), poly(isobutyl methacrylate), poly(tert-butyl methacrylate), poly(n-propyl methacrylate), poly(isopropyl methacrylate), poly(ethyl methacrylate), poly(methyl methacrylate), epoxy resins, polyurethanes, rayon, rayon-triacetate, cellulose acetate, cellulose butyrate, cellulose acetate butyrate, cellophane, cellulose nitrate, cellulose propionate, cellulose ethers, carboxymethyl cellulose, polyethers such as poly(ethylene glycol) (PEG), copoly(ether-esters) (e.g. poly(ethylene oxide-co-lactic acid) (PEO/PLA)), polyalkylene oxides such as poly(ethylene oxide), poly(propylene oxide), poly(ether ester), polyalkylene oxalates, phosphoryl choline containing polymer, choline, poly(aspirin), polymers and co-polymers of hydroxyl bearing monomers such as 2-hydroxyethyl methacrylate (HEMA), hydroxypropyl methacrylate (HPMA), hydroxypropylmethacrylamide, PEG acrylate (PEGA), PEG methacrylate, methacrylate polymers containing 2-methacryloyloxyethyl-phosphorylcholine (MPC) and n-vinyl pyrrolidone (VP), carboxylic acid bearing monomers such as methacrylic acid (MA), acrylic acid (AA), alkoxymethacrylate, alkoxyacrylate, and 3-trimethylsilylpropyl methacrylate (TMSPMA), poly(styrene-isoprene-styrene)-PEG (SIS-PEG), polystyrene-PEG, polyisobutylene-PEG, polycaprolactone-PEG (PCL-PEG), PLA-PEG, poly(methyl methacrylate)-PEG (PMMA-PEG), polydimethylsiloxane-co-PEG (PDMS-PEG), poly(vinylidene fluoride)-PEG (PVDF-PEG), PLURONIC™ surfactants (polypropylene oxide-co-polyethylene glycol), poly (tetramethylene glycol), hydroxy functional poly(vinyl pyrrolidone), biomolecules such as collagen, chitosan, alginate, fibrin, fibrinogen, cellulose, starch, dextran, dextrin, hyaluronic acid, fragments and derivatives of hyaluronic acid, heparin, fragments and derivatives of heparin, glycosamino glycan (GAG), GAG derivatives, polysaccharide, elastin, elastin protein mimetics, or combinations thereof. Some examples of elastin protein mimetics include (LGGVG)$_n$, (VPGVG)$_n$, Val-Pro-Gly-Val-Gly, or synthetic biomimetic poly(L-glytanmate)-b-poly(2-acryloyloxyethyllactoside)-b-poly(1-glutamate) triblock copolymer.

Presently preferred polymers for the fabrication of drug reservoir layers comprising mTOR inhibitors of this invention include, without limitation, poly(vinylidene fluoride) (PVDF), poly(vinylidene fluoride-co-hexafluoropropylene) (PVDF-HFP), poly(vinylidene fluoride-co-chlorotrifluoroethylene) (PVDF-CTFE), poly(vinylidene fluoride-co-hexafluoropropylene-co-tetrafluoroethylene), poly(vinylidene fluoride-co-tetrafluoroethylene) (PVDF-TFE), and combinations thereof. It is presently preferred that the polymer have at least 25% vinylidene fluoride by weight. For the purposes of this invention a vinylidene fluoride containing polymer having a weight average molecular weight of from about 40,000 to about 750,000 Daltons is presently preferred. To function optimally as a stent coating, a polymer must satisfy several criteria. Vinylidene fluoride based polymers can have both good elongation properties to accommodate stent expansion, as well as good toughness to withstand the rigors of stent crimping and delivery to a lesion site. This family of polymers has, in general, a sub-ambient glass transition temperature and can be formulated to provide for controlled drug release. They are very stable polymers due to a polymer backbone of only carbon-carbon bonds with all pendant bonds being either C—H or C—F. This confers great chemical stability during processing and in vivo. The long-term biocompatibility tends to be good for this class of polymers due to their purity and lack or reactivity. In addition, fluorinated surfaces provide good thrombo-resistance/hemocompatibility.

If desired, or if necessary to obtain the desired release rate, other polymers may be blended with the above fluoropolymers. In particular, poly(n-butyl methacrylate) may advantageously be blended with the fluoropolymers to modify mTOR inhibitor release rates.

In addition to the composition of polymeric matrix in which the mTOR inhibitor is formulated, the drug-to-polymer (D/P) ratio in each layer will significantly affect how quickly the incorporated mTOR inhibitor will be released. In general, the higher the D/P ratio, the sooner the mTOR inhibitor will be released. The D/P ratio may be varied from about 1:30 to about 1:1 for the purposes of this invention. Most preferred at present are D/P ratios of about 4:1 to about 1:1.

The thickness of each of the drug reservoir layer will, of course, also affect the release of the mTOR inhibitor. The thicker the layer the more slowly will the mTOR inhibitor be released. Suitable reservoir layer thickness may be directly calculated once the desired release rate, drug loading in $\mu g/cm^2$ and drug/polymer (D/P) ratio are established. For example, with regard to everolimus, the "normal" loading is approximately 100 $\mu g/cm^2$ total solids. The D/P is 1:1 and the release rate is about 90% over one to three months so, given these parameters, it would be readily determined by one skilled in the art that a suitable reservoir layer thickness would be about 0.75 to 1.25 $\mu m$.

Finally, the presence of absence of separate drug release timing layers between the each of the drug reservoir layers and the external environment will also affect the rate of release and overall timing of full release of the mTOR inhibitor form each drug reservoir layer. The technology of drug release timing layers is well understood in the art. The skilled artisan will be able to formulate such timing layers, whether necessary or simply desirable to achieve a certain release rate, based on the disclosure herein, without difficulty.

In fact, the formulation of drug reservoir layers with specific drug-release properties is in general well within the knowledge of the skilled artisan and the preparation of implantable medical devices with the drug release characteristics presented in this disclosure will readily achieved by that practitioner of the art based on the disclosures herein and need not be further explicated.

Since this invention requires that the different drug dose density drug reservoir layers release their content over specific time periods, the possible migration of drug from one layer to another, which could negatively affect the intended release profile, is preferably avoided. Layer-to-layer drug infiltration would be most likely to occur over longer periods of time such as those encountered when the finished devices are placed on the shelf awaiting use. While it may be empirically determined that such is not the case and the drugs pretty much stay where they were intended to be, if such is not the case, the use of barrier layers between the drug reservoir layers might be warranted. Such barrier layers would preferably be completely or nearly completely impermeable to the drug until a particular event occurs such as the wetting of the barrier layer upon implantation in a patient. Many polymers are known that have the required quality: they are impermeable until moistened and then they are essentially completely permeable so as to not detrimentally affect the intended drug releases. While numerous biocompatible polymers that could serve as barrier layers, and all such polymers are within the scope of this invention, polymers that can be used include, without limitation, blends of poly(ethylene-co-vinyl alcohol) or poly(N-vinylpyrrolidine) with poly(n-butyl methacrylate) in various proportions.

While the administration of an increased dose of an mTOR inhibitor alone should suffice to beneficially reduce or substantially eliminate the need for TLR and its attendant MACE risk, inclusion of an anti-inflammatory agent along with the mTOR inhibitor would be expected to also provide a beneficial effect and such is an embodiment of this invention.

Suitable anti-inflammatory agents that can be used in combination with the mTOR inhibitor of this invention include, without limitation, clobetasol, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, deflazacort, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, methylprednisolone suleptanate, morniflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus, pimecorlimus and prodrugs, co-drugs and combinations thereof.

Presently preferred anti-inflammatory agents for use in the present invention are dexamethasone and clobetasol. Derivatives of dexamethasone such as, without limitation, dexamethasone acetate, dexamethasone laurate, dexamethasone-tert-butylacetate, dexamethasone tetrahydrophthalate, and dexamethasone isonicotinate might also be used.

With regard to either dexamethasone or clobetasol, the dose density of the agent on a device of this invention would be relatively low so as to avoid the potential negative effects of anti-inflammatory agents discussed previously herein. Dexamethasone is generally classified under the heading of low potency corticosteroids based on clinical studies and vasomotor assays. To the contrary, clobetasol is characterized on the same terms as a very high or super high potency corticosteroid. Thus, the loading density of dexamethaxone or derivative thereof into a drug reservoir layer of a device of this invention can range generally from about 20 $\mu g/cm^2$ to about 200 $\mu g/cm^2$. On the other hand, the loading density of clobetasol is substantially lower, ranging from about 1.0 $\mu g/cm^2$ to about 10 $\mu g/cm^2$.

As a non-limiting example, a device of this invention could include dexamethasone at a dose density of about 25 $\mu g/cm^2$ in the early release drug reservoir layer, about 200 $\mu g/cm^2$ in the mid release drug reservoir layer and about 50 $\mu g/cm^2$ in the late release drug reservoir layer.

On the other hand, if clobetasol is used, a device of this invention might include about 10 $\mu g/cc^2$ in the early release drug reservoir layer, about 1.0 $\mu g/cm^2$ in the mid release drug reservoir layer and none in the late release drug reservoir layer.

Curtailment of SMC proliferation can be assisted by concurrent enhancement of re-endothelialization. RGD peptides, in particular, cyclic RGD peptides are known to increase endothelialization and therefore including them in one or more of the drug reservoir layers would be expected to be beneficial in reducing events leading to TLR. As yet another non-limiting example, a device of this invention might include, along with the mTOR inhibitor and, optionally, the anti-inflammatory agent, 250 $\mu g/cm^2$ of cRGD in the outermost or early release drug reservoir layer, about 100 $\mu g/cm^2$ of cRGD in the mid release drug reservoir layer and about 75 $\mu g/cm^2$ in the late release or outermost drug reservoir layer.

The release rate of the mTOR inhibitor, the anti-inflammatory agent and the RGD peptide from an implantable medical device is such that about 80% to about 99% of the agents are released from each layer over the indicated time span for release from that particular layer; i.e., 0-7 days, 8-29 days or 30 to 180 days. It is presently preferred that at least 95% of each drug is released from each layer within that layer's indicated time period. Optionally, each reservoir layer can include a blank, drug-free polymer layer as a release rate control layer with a thickness of between about 0.75 and about 4.0.

In another embodiment, all the coating layers described above may comprise absorbable polymers such as, without limitation, poly(D,L-lactide) and may be applied over a bioabsorbable vascular scaffold (BVS).

In yet another embodiment, the BVS can be fabricated form brained low density poly(L-lactic acid) (LPLLA) fibers, wherein the fibers are loaded with dexamethasone by co-extruding the dexamethasone with the LPLLA at a ratio of 1:10 to 1:3. The braided BVS is then coated with the coating layers described above.

What is claimed:

1. An implantable medical device for treatment of vascular disease in a diabetic patient, comprising:
    a device body; and
    three drug reservoir layers disposed over the device body, wherein each layer comprises an mTOR inhibitor and at least one of the three layers comprises at least 200 $\mu g/cm^2$ of an mTOR inhibitor; wherein
        the first drug reservoir layer, which is the outermost of the drug reservoir layers, releases at least 80% of its mTOR inhibitor over about 7 days post implantation of the device;
        the second drug reservoir layer, which is disposed beneath the first drug reservoir layer, releases at least 80% of its mTOR inhibitor over about 22 days beginning at about day 8 post implantation of the device; and
        the third drug reservoir layer, which is disposed beneath the second drug reservoir layer, releases at least 80% of its mTOR inhibitor over about 150 days beginning at about day 30 post implantation.

2. The implantable medical device of claim 1, wherein:
    the first drug reservoir layer comprises about 100 $\mu g/cm^2$ to about 200 $\mu g/cm^2$ of its mTOR inhibitor;
    the second drug reservoir layer comprises about 200 $\mu g/cm^2$ to about 800 $\mu g/cm^2$ of its mTOR inhibitor; and
    the third drug reservoir layer comprises about 20 to about 100 $\mu g/cm^2$ of its mTOR inhibitor.

3. The implantable medical device of claim 1, wherein:
    the first drug reservoir layer comprises about 100 $\mu g/cm^2$ of its mTOR inhibitor;
    the second drug reservoir layer comprises about 500 $\mu g/cm^2$ of its mTOR inhibitor; and
    the third drug reservoir layer comprises about 100 $\mu g/cm^2$ of its mTOR inhibitor.

4. The implantable medical device of claim 1, wherein:
    the first drug reservoir layer comprises about 200 $\mu g/cm^2$ of its mTOR inhibitor;
    the second drug reservoir layer comprises about 300 $\mu g/cm^2$ of its mTOR inhibitor; and
    the third drug reservoir layer comprises about 20 $\mu g/cm^2$ of its mTOR inhibitor.

5. The implantable medical device of claim 1, wherein the mTOR inhibitor is selected from a group consisting of everolimus, zotarolimus, sirolimus, biolimus, myolimus, novolimus, temsirolimus, deforolimus and combinations thereof.

6. The implantable medical device of claim 1, further comprising an anti-inflammatory agent in the first drug reservoir layer, in the second drug reservoir layer, in the third drug reservoir layer or in any combination thereof.

7. The implantable medical device of claim 6, wherein the anti-inflammatory agent is selected from the group consisting of dexamethasone, dexamethasone acetate, dexamethasone laurate, dexamethasone-tert-butylacetate, dexamethasone tetrahydrophthalate, dexamethasone isonicotinate and clobetasol.

8. The implantable medical device of claim 7, wherein at least one of the drug reservoir layers comprises 20 to 200

μg/cm² of the dexamethasone, dexamethasone acetate, dexamethasone laurate, dexamethasone-tert-butylacetate, dexamethasone tetrahydrophthalate, or dexamethasone isonicotinate.

9. The implantable medical device of claim 7, wherein at least one of the drug reservoir layers comprises 1 to 10 μg/cm² of the clobetasol.

10. The implantable medical device of claim 1, further comprising an RGD peptide, a c-RGD peptide or an RGD peptide mimetic in the first drug reservoir layer, in the second drug reservoir layer, in the third drug reservoir layer or in any combination thereof.

11. The implantable medical device of claim 6, further comprising an RGD peptide, a c-RGD peptide or an RGD peptide mimetic in the first drug reservoir layer, in the second drug reservoir layer, in the third drug reservoir layer or in any combination thereof.

12. The implantable medical device of claim 1, further comprising a barrier layer between the first drug reservoir layer and the external environment, between the first drug reservoir layer and the second drug reservoir layer, between the second drug reservoir layer and the third drug reservoir layer or any combination of the foregoing.

13. The implantable medical device of claim 1, wherein the implantable medical device is a stent.

14. A method of treating a human with a vascular disorder and type I or type II diabetes comprising, implanting a stent in the human having a vascular disorder and type I or type II diabetes, the stent comprising at least 520 μg/cm² of an mTOR inhibitor selected from a group consisting of everolimus, zotarolimus, sirolimus, biolimus, myolimus, novolimus, temsirolimus, deforolimus and combinations thereof.

15. The method of claim 14, wherein the stent further comprises an anti-inflammatory agent selected from the group consisting of dexamethasone, dexamethasone acetate, dexamethasone laurate, dexamethasone-tert-butylacetate, dexamethasone tetrahydrophthalate, dexamethasone isonicotinate and clobetasol.

16. The method of claim 15, wherein the dexamethasone, dexamethasone acetate, dexamethasone laurate, dexamethasone-tert-butylacetate, dexamethasone tetrahydrophthalate, or dexamethasone isonicotinate is present in an amount of 20 to 200 μg/cm².

17. The method of claim 15, wherein the clobetasol is present in an amount of 1 to 10 μg/cm².

* * * * *